US005538943A

United States Patent [19]

Naef et al.

[11] Patent Number: 5,538,943

[45] Date of Patent: Jul. 23, 1996

[54] USE OF 1,3-UNDECADIEN-5-YNE AS A PERFUMING INGREDIENT

[75] Inventors: Ferdinand Naef, Carouge; René Decorzant, Onex; Sina D. Escher, Confignon, all of Switzerland; Jean-Marc Gaudin, Annemasse, France; Pierre-Alain Blanc, Crassier, Switzerland

[73] Assignee: Firmenich SA, Geneva, Switzerland

[21] Appl. No.: 446,344

[22] Filed: May 22, 1995

[30] Foreign Application Priority Data

Jul. 28, 1994 [CH] Switzerland .......................... 2386/94

[51] Int. Cl.[6] .................................................... A61K 7/46

[52] U.S. Cl. ............................................................... 512/1

[58] Field of Search ................................................ 512/1

[56] References Cited

PUBLICATIONS

B. Andreini et al., Highly Stero–and Regioselective Palladium–Catalyzed Synthesis of (3E,5Z)–(3E,5E)–, and (3Z, 5E)–1,3,5–Undecatriene, *Tetrahedron*, vol. 43, No. 20, pp. 4591–4600, 1987.

fF. Naef et al., The Four Isomeric 1,3,5–Undecatrienes–Synthesis and Configurational Assignemtn, *Helveticachimica Acta*, vol. 58, FASC. 4, pp. 1016–1037, 1975.

*Primary Examiner*—James H. Reamer
*Attorney, Agent, or Firm*—Pennie & Edmonds

[57] ABSTRACT

1,3-Undecadien-5-yne and its (E) and (Z) configuration isomers are useful perfuming ingredients for the preparation of perfuming bases and a variety of perfumed consumer products, to which they impart odor characters of the galbanum, floral, fruity-citrus type.

9 Claims, No Drawings

USE OF 1,3-UNDECADIEN-5-YNE AS A PERFUMING INGREDIENT

BRIEF SUMMARY OF THE INVENTION

The present invention relates to the perfume industry. It concerns, more particularly, the use of 1,3-undecadien-5-yne as a perfuming ingredient, for preparing perfuming compositions and perfumed articles.

Thus, one object of the present invention is a perfuming composition or a perfumed article containing as an active perfuming ingredient 1,3-undecadien-5-yne.

The invention also concerns a perfume or cologne, a soap, a bath or shower gel, a shampoo or other hair-care product, a cosmetic preparation, a body deodorant, an air-freshener, a detergent or a fabric softener, or a household product, which contains as an active perfuming ingredient 1,3-undecadien-5-yne.

A further object of the invention is a method to confer, improve, enhance or modify the odor properties of a perfuming composition or of a perfumed article, which method comprises adding to said composition or article a fragrance effective amount of 1,3-undecadien-5-yne.

BACKGROUND AND DETAILED DESCRIPTION OF THE INVENTION

The compound above-cited is well-known as a chemical entity. It has in fact been repeatedly cited as a useful intermediate in the synthesis of 1,3,5-undecatriene and its isomers [see, for example, B. P. Andreini et al., Tetrahedron 43, 4591 (1987); F. Näf et al., Helv. Chim. Acta, 58, 1016 (1975)]. In spite of this, there has been no mention, nor even suggestion, in any of these references of the possible utility of this compound, or of one of its stereoisomers, for perfumery applications.

Yet, we have now established that 1,3-undecadien-5-yne and its (E) and (Z) configuration isomers possess very useful odors, and that they are capable of creating floral, green and galbanum type odor effects. Thus, (E)-1,3-undecadien-5-yne turns out to be a choice perfuming ingredient, possessing a remarkably powerful odor with a galbanum and fruity character, reminiscent of the odor of mandarine peel, together with a distinct note similar to that which is characteristic of methyl octynecarbonate and methyl heptynecarbonate. It is in fact a very pleasant odor note, which recalls the odor of violet leaves, while also possessing a green and fruity character reminiscent of the odor of Dynascone® [1-(5,5 -dimethyl-1-cyclohexen-1-yl)-4-penten-1-one; origin: Firmenich SA, Geneva, Switzerland] though less allylic and with a more pronounced galbanum character, accompanied by a very clean citrus-mandarine subnote. The use of this compound in perfumery is thus a preferred embodiment of the invention.

On the other hand, (Z)-1,3-undecadien-5-yne is also a useful perfuming ingredient, but it possesses a greener odor, with a more pronounced mastic-ocimene character.

As a result of their odor qualities, these compounds can therefore find wide use in perfumery, namely for the preparation of perfuming bases and concentrates, perfumes and colognes, as well as for perfuming a variety of consumer products such as soaps, bath or shower gels, shampoos and other hair-care products, cosmetic preparations, body deodorants, air-fresheners, or yet detergents, fabric softeners or household products.

In these applications, they can be used in a pure state or, as is more common, in admixture with other perfuming co-ingredients, solvents or adjuvants of current use in perfumery and which can be easily selected by the skilled person as a function of the fragrance effect that is desired to achieve and of the nature of the product to be perfumed. A more detailed description of such ingredients is not warranted here and examples thereof can be found in the reference works and specialized textbooks of the type of that of S. Arctander, Perfume & Flavor Chemicals, Montclair, N.J., U.S.A. (1969), for example.

A particular embodiment of the invention consists in the use of the compound cited in the form of a mixture of the two stereoisomers (E) and (Z), wherein the relative proportions (E)/(Z) can vary in a wide range of values, typically from 1:0 to 0:1, and can assume any intermediate value between these limits. Preferred embodiments relate to the use of such mixtures of (E)-1,3-undecadien-5-yne and (Z)-1,3-undecadien-5-yne, wherein the first mentioned isomer is present in an amount of 50% by weight or more, relative to the weight of said mixture.

The concentrations in which these compounds, and their mixtures above-mentioned, can be used to achieve the desired perfuming effects vary in a wide range of values, since they are dependent on the nature of the product to be perfumed and on the type of odor effect that one desires to obtain. In addition, they are also a function of the nature of the other co-ingredients present in a given composition. By way of example, one can however cite concentration values of the order of 0.5 to 5%, or even 10% or more by weight of said compound, relative to the weight of the composition, as convenient proportion values whenever 1,3-undecadien-5-yne or its isomers are added to perfuming bases and concentrates. Much lower concentration values will typically be necessary when using these compounds for perfuming the various consumer articles cited above.

As previously mentioned, the synthesis of 1,3-undecadien-5-yne and its two stereoiomers has been described before, namely by F. Näf et al. in the reference cited above.

The invention thus relates to the compositions and perfumed products above-cited, which contain these compounds as active perfuming ingredients, as well as to the method of use of said compounds to impart, enhance, improve or modify the odor of these compositions and products, which method comprises adding thereto 1,3-undecadien-5-yne, one of its stereoisomers or a mixture of the latter. The invention is illustrated in further detail by way of the following examples.

EXAMPLE 1

Perfuming composition

A base perfuming composition was prepared by admixing the following ingredients:

| Ingredients | Parts by weight |
|---|---|
| 10%* Geranyl acetate | 10 |
| Linalyl acetate | 15 |
| Bergamot essential oil | 120 |
| Cedroxyde ®[1)] | 95 |
| California lemon essential oil | 20 |
| Coumarine | 10 |
| Dihydromyrcenol[2)] | 40 |
| Exaltolide ®[3)] | 55 |
| Galaxolide ® 50[4)] | 95 |

-continued

| Ingredients | Parts by weight |
|---|---|
| Hedione ®[5)] | 40 |
| 10%** Indol | 5 |
| 1%* Isobutylquinoleine[6)] | 20 |
| Lyral ®[7)] | 45 |
| Mandarine essential oil | 55 |
| 10%* Crystalmoss | 30 |
| Nutmeg essential oil | 10 |
| 10%* trans-1-[2,2,6-Trimethyl-1-cyclohexyl]-3-hexanol[8)] | 15 |
| Patchouli essential oil | 15 |
| Polysantol ®[9)] | 5 |
| Polywood ®[10)] | 190 |
| Amyl salicylate | 15 |
| Triplal ®[11)] C | 5 |
| 1%* γ-Undecalactone | 10 |
| 10%* β-Ionone | 10 |
| Total | 930 |

*in dipropyleneglycol (DIPG)
**in triethanolamine
1)trimethyl 13-oxabicyclo[10.1.0]trideca-4,8-diene; origin: Firmenich SA, Geneva, Switzerland
2)2,6-dimethyl-7-octen-2-ol; origin: International Flavors & Fragrances, USA
3)cyclopentadecanolide; origin: Firmenich SA, Geneva, Switzerland
4)1,3,4,6,7,8-hexahydro-4,6,6,7,8,8-hexamethyl-cyclopenta[g]isochromene: origin: International Flavors & Fragrances, USA
5)methyl dihydrojasmonate; origin: Firmenich SA, Geneva, Switzerland
6)origin: International Flavors & Fragrances, USA
7)4-(4-hydroxy-4-methyl-pentyl)-3-cyclohexene-1-carboxaldehyde; origin: International Flavors & Fragrances, USA
8)origin: Firmenich SA, Geneva, Switzerland
9)3,3-dimethyl-5-(2,2,3-trimethyl-3-cydopenten-1-yl)-4-penten-2-ol; origin: Firmenich SA, Geneva, Switzerland
10)perhydro-5,5,8a-trimethyl-2-naphthyl acetate; origin: Firmenich SA, Geneva, Switzerland
11)2,4-dimethyl-3-cyclohexene-1-carboxaldehyde; origin: International Flavors & Fragrances, USA Upon adding to this base composition of the woody, musky, floral type 70 parts by weight of a 10% solution in DIPG of (E)-1,3-undecadien-5-yne, there was obtained a novel composition with a very marked green and violet leaves odor character. The addition of this compound had also distinctly exhalted the fresh, citrus type note and, in particular, the mandarine odor character of the composition.

EXAMPLE 2

Perfuming composition for a fabric softener

A base perfuming composition intended for use in a fabric softener was prepared by admixing the following ingredients:

| Ingredients | Parts by weight |
|---|---|
| Benzyl acetate | 55 |
| Carbinol acetate | 25 |
| 1%* cis-3-Hexenyl acetate | 30 |
| Citronellyl acetate | 5 |
| p-tert-Butyl-cyclohexyl acetate | 45 |
| Anisic aldehyde | 5 |
| Hexylcinnamic aldehyde | 60 |
| Citronellol | 55 |
| 10%* γ-Decalactone | 15 |
| 50% β-Damascone in ethyl citrate | 10 |
| 10%* Ethylvanilline | 5 |
| Exaltex ®[1)] | 30 |
| Geraniol | 75 |
| Galaxolide ® 50[2)] | 40 |
| 10%* α-Ionone | 20 |
| 1%* Isobutylquinoleine[3)] | 25 |
| Phenylethyl isobutyrate | 5 |
| Iralia ®[4)] | 25 |
| Lilial ®[5)] | 35 |
| Linalol | 35 |

-continued

| Ingredients | Parts by weight |
|---|---|
| Lyral ®[6)] | 15 |
| Methylnaphthyl ketone cryst. | 10 |
| 10%* Crystalmoss | 10 |
| Phenethylol | 170 |
| Polysantol ®[7)] | 5 |
| Verdyl propionate | 20 |
| 10%* Rosalva ®[8)] | 5 |
| Rosinol cryst. | 25 |
| Amyl salicylate | 60 |
| Hexyl salicylate | 50 |
| Ylang synth. | 20 |
| Total | 990 |

*in DIPG
1)pentadecanolide; origin: Firmenich SA, Geneva, Switzerland
2)see Example 1
3)see Example 1
4)methylionone; origin: Firmenich SA, Geneva, Switzerland
5)2-methyl-3-(4-tert-butyl-1-phenyl)-propanal; origin: Givaudan-Roure, Vernier, Switzerland
6)see Example 1
7)see Example 1
8)9-decen-1-ol; origin: International Flavors & Fragrances, USA To this base composition of the floral, rosy, powdery, violet type there were added 10 parts by weight of a 10% solution in DIPG of (E)-1,3-undecadien-5-yne. We thus obtained a novel composition whose floral-violet type note, typically imparted by Iralia® and α-ionone, was distinctly enhanced. Furthermore, the odor of the composition had thus become more greenfruity, with a slight liquourish connotation, the effect of which was particularly pleasant on the wet linen which had been treated with a fabric softener containing about 0.1% weight of this novel composition.

What we claim is:

1. A perfuming composition or a perfumed article containing as an active perfuming ingredient 1,3-undecadien-5-yne together with a perfuming co-ingredient.

2. The perfuming composition or perfumed article of claim 1, wherein 1,3-undecadien-5-yne is present in the form of one of its (E) or (Z) configuration isomers, or of any mixture of these two isomers.

3. The perfuming composition or perfumed article of claim 2, wherein said mixture contains 50% or more by weight of (E)-1,3-undecadien-5-yne, relative to the weight of the mixture.

4. A perfume or cologne, a soap, a bath or shower gel, a shampoo or other hair-care product, a cosmetic preparation, a body deodorant, an air-freshener, a detergent or a fabric softener, or a household product, which contains as an active perfuming ingredient 1,3-undecadien-5-yne.

5. A method to confer, improve, enhance or modify the odor properties of a perfuming composition or of a perfumed article, which method comprises adding to said composition or article a fragrance effective amount of 1,3-undecadien-5-yne.

6. The method of claim 5, wherein 1,3-undecadien-5-yne is used in the form of its (E) or (Z) configuration isomer, or in the form of any mixture of these two isomers.

7. The method of claim 6, wherein said mixture contains 50% or more by weight of (E)-1,3-undecadien-5-yne, relative to the weight of the mixture.

8. The composition of claim 1 wherein the perfuming co-ingredient is a solvent.

9. The composition of claim 1 wherein the perfuming co-ingredient is an adjuvant of current use in perfumery.

* * * * *